(12) United States Patent
Etlin et al.

(10) Patent No.: US 7,612,202 B2
(45) Date of Patent: Nov. 3, 2009

(54) PROCESS FOR PREPARING TEMOZOLOMIDE

(75) Inventors: Olga Etlin, Beer-Sheva (IL); Mohammed Alnabari, Hura (IL); Yana Sery, Beer-Sheva (IL); Edna Danon, Meitar (IL); Oded Arad, Rechovot (IL); Joseph Kaspi, Givatayim (IL)

(73) Assignee: Chemagis, Ltd., Bnei Brak (IL)

( * ) Notice: Subject to any disclaimer, the term of this patent is extended or adjusted under 35 U.S.C. 154(b) by 496 days.

(21) Appl. No.: 11/354,899

(22) Filed: Feb. 16, 2006

(65) Prior Publication Data

US 2006/0183898 A1 Aug. 17, 2006

Related U.S. Application Data

(60) Provisional application No. 60/735,828, filed on Nov. 14, 2005, provisional application No. 60/653,528, filed on Feb. 17, 2005.

(51) Int. Cl.
*C07D 487/04* (2006.01)
*A61K 31/395* (2006.01)
*A61P 35/00* (2006.01)

(52) U.S. Cl. .................................... 544/179
(58) Field of Classification Search ............... 544/179
See application file for complete search history.

(56) References Cited

U.S. PATENT DOCUMENTS

| 5,260,291 | A | 11/1993 | Lunt et al. |
| 6,844,434 | B2 | 1/2005 | Kuo |
| 2002/0095036 | A1 * | 7/2002 | Kuo et al. .............. 544/179 |
| 2005/0187206 | A1 | 8/2005 | Adin et al. |

FOREIGN PATENT DOCUMENTS

WO  WO 2005/063757 A2  7/2005

OTHER PUBLICATIONS

LanXess Engineering Chemistry, Lewatit Resin, Lewatit Mono Plus MP 64,Production Information, pp. 1-4, 2007.*
Remco Engineering Ion Exchange Chemistry and Operation, 1-11, 2008.*
Wang et al., J. Org. Chem. 62(21), 7288-7294, 1997.*
Wang et al. "Alternative Syntheses of the Antitumour Drug Temozolomide Avoiding the Use of Methyl Isocyanate", Journal of the Chemical Society, Chemical Communication, p. 1687-1688, 1994.
Clark et al. "Antitumor Imidazotetrazines. 32. Synthesis of Novel Imidazotetrazinones and Related Bicyclic Heterocycles to Probe the Mode of Action of the Antitumor Drug Temozolomide", Journal of Medicinal Chemistry, 38(9): 1493-1504, 1995.
Stevens et al. "Antitumor Imidazotetrazines. 1. Synthesis and Chemistry of 8-Carbamoyl-3-(2-Chloroethyl)Imidazo[5,1-D]-1,2,3,5-Tetrazin-4(3H)-One, A Novel Broad-Spectrum Antitumor Agent", Journal of Medicinal Chemistry, 27(2): 196-201, 1984.
Baig et al. "Antitumour Imidazotetrazines. Part 12. Reactions of Mitozolomide and Its 3-Alkyl Congeners With Oxygen, Nitrogen, Halogen, and Carbon Nucleophiles", J. Chem. Soc. Perkin Trans., I: 675-670, 1987.
Newlands et al. "Temozolomide: A Review of Its Discovery, Chemical Properties, Pre-Clinical Development and Clinical Trials", Cancer Treatment Reviews, 23: 35-61, 1997.
Brown et al. "Antitumor Imidazotetrazines. 40. Radiosyntheses of [4-11C-Carbonyl]- and [3-N-11C-Methyl]-8-Carbamoyl-3-Methylimidazo[5,1-D]-1,2,3,5-Tetrazin-4(3H)-One (Temozolomide) for Positron Emission Tomography (PET) Studies", Journal of Medicinal Chemistry, 45(25): 5448-5457, 2002.
Wang et al., "Preparation and Thermostability of Polymorphs of Temozolomide," *Chinese Journal of Pharmaceuticals*, vol. 34(4), pp. 178-180 (2003). abstract.
Wanner et al., "A new synthesis of temozolomide," *J. Chem. Soc. Perkins Trans I*, pp. 1877-1880 (2002).

* cited by examiner

*Primary Examiner*—Venkataraman Balasubramanian
(74) *Attorney, Agent, or Firm*—Leydig, Voit & Mayer, Ltd.

(57) ABSTRACT

The present invention provides a process for preparing highly pure Temozolomide base which includes recovery from the purification mother liquors by using an anionic exchange resin. By treating Temozolomide hydrochloride with a mixture of an organic acid, a water miscible organic solvent, and water, Temozolomide free base is obtained in an acidic medium. Due to the high sensitivity of Temozolomide to basic pH values the recovery-including process is especially advantageous because it enables obtaining high yields of highly pure Temozolomide base in acidic conditions.

The process for producing Temozolomide base includes hydrolysis of the starting material 8-cyano-3-methyl-[3H]-imidazo[5,1-d]-tetrazin-4-one in acidic medium to obtain highly pure Temozolomide hydrochloride in high yield.

26 Claims, No Drawings

PROCESS FOR PREPARING TEMOZOLOMIDE

RELATED APPLICATIONS

The present application claims the benefit of U.S. Provisional Patent Application No. 60/653,528, filed on Feb. 17, 2005, and U.S. Provisional Patent Application No. 60/735,828, filed on Nov. 14, 2005, the contents of which are incorporated herein by reference.

FIELD OF THE INVENTION

The present invention relates to an improved process for preparing Temozolomide in high purity and yield via hydrolysis of the starting material 8-cyano-3-methyl-[3H]-imidazo[5,1-d]-tetrazin-4-one, then converting the Temozolomide hydrochloride obtained to Temozolomide free base in acidic medium, thus avoiding the high sensitivity of Temozolomide at non acidic pH values.

BACKGROUND OF THE INVENTION

Temozolomide is the international non-proprietary name used to identify 8-carbamoyl-3-methyl-imidazo[5,1-d]-1,2,3,5-tetrazin-4(3H)-one (I):

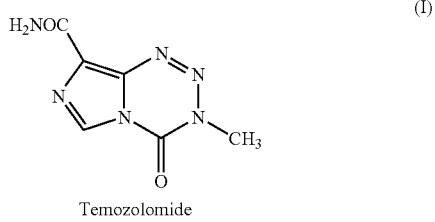

Temozolomide

Temozolomide is an antitumor agent indicated for treating patients with malignant glioma such as cancer, breast cancer, refractory anaplastic astrocytoma, i.e., patients at first relapse who have experienced disease progression in malignant glioma, glioblastoma multiform and anaplastic astrocytoma, on a drug regimen containing a nitrosourea and procarbazine.

Temozolomide preparations are sold on the US market as hard capsules containing 5 mg, 20 mg, 100 mg or 250 mg Temozolomide (marketed as Temodar® by Schering Corporation, Kenilworth, N.J., USA). In other markets it is sold as Temodal®.

Temozolomide is stable at acidic pH (<5), and labile at pH>7, hence can be administered orally. Temozolomide is spontaneously hydrolyzed at physiologic pH to the active species 5-(3-methyltriazen-1-yl)imidazole-4-carboxamide (MTIC) and to the Temozolomide acid metabolite 3-methyl-2,3-dihydro-4-oxoimidazo-[5,1-d]-tetrazine-8-carboxylic acid (TMA).

MTIC is further fragmented to 5-aminoimidazole-4-carboxamide (AIC) and to methyl-diazonium cation, which is a proximal DNA methylating agent. It is proposed in an article by Clark A. S., Deans B., Stevens M. F. G., Tisdale M. J., Wheelhouse R. T., Denny B. J, and Hartley J. A. titled "Antitumor imidazotetrazines. 32. Synthesis of novel imidazotetrazinones and related bicyclic heterocycles to probe the mode of action of the antitumor drug Temozolomide", published in J. Med. Chem. 38, 1493-1504 (1995), that a sequence of guanine residues represents an accessible nucleophilic and basic microenvironment in DNA, which would facilitate sequence-selective conversion of Temozolomide to MTIC.

The hydrophobic nature of MTIC enables it to penetrate the blood-brain-barrier membrane, therefore the drug is extensively used to treat also malignant brain tumors. The conversion of Temozolomide to MTIC and the further breakdown of MTIC to AIC and a methyl-diazonium cation is irreversible and pH-dependent. In aqueous buffers, Temozolomide is stable at pH<5, but rapidly decomposes to MTIC at pH>7; in contrast, MTIC is stable at alkaline pH, but rapidly breaks down to AIC at pH<7. Temozolomide has an in vitro half-life of 1.9 hours in phosphate buffer at 37° C. and pH 7.4, whereas MTIC in the same solution has a half-life of about 2 minutes, (see for example, Denny B. J., Wheelhouse R. T., Stevens M. F. G., Lincoln L., and Slack J. A. "NMR and molecular modeling investigation of the mechanism of activation of the antitumor drug Temozolomide and its interaction with DNA", Biochemistry, 1994, 33, 9045-9051).

A small percentage (about 2%) of an administered Temozolomide dose is metabolized to TMA, the carboxylic acid analogue of Temozolomide (Tsang L. L. H., Farmer P. B., Gescher A., Slack J. A., in "Characterization of urinary metabolites of temozolomide in humans and mice and evaluation of their cytotoxicity", Cancer Chemother. Pharmacol., 26: 429-436, 1990).

Scheme 1 below depicts the proposed metabolism and degradation pathways of Temozolomide. The sign * shows the position of the $^{14}C$-labeled carbon atom. Clinical trials that have been carried out with $^{14}C$-Temozolomide showed that the drug is converted to MTIC under physiological conditions, by a non-enzymatic chemical degradation process. (S. D Baker et al. in "Absorption, metabolism, and excretion of $^{14}C$-Temozolomide following oral administration to patients with advanced cancer", Clinical Cancer Research, Vol. 5, 309-317, 1999)

Scheme 1

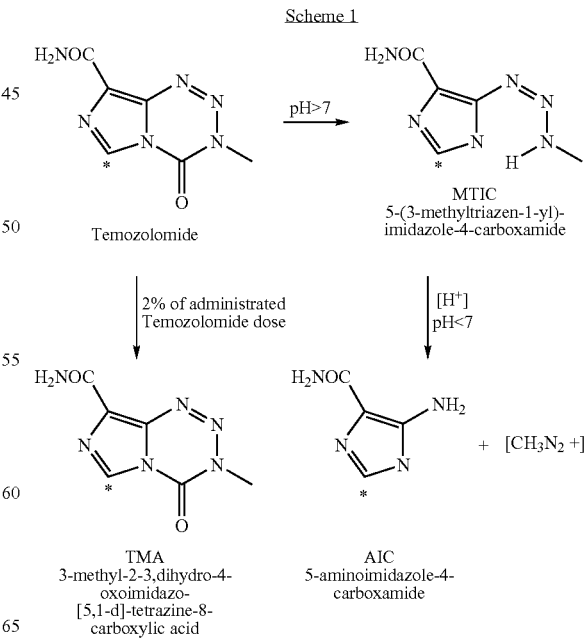

The reactivity of anti-tumor imidazotetrazines such as Temozolomide in organic systems is completely different from the reactivity in aqueous media and is dominated by retro-cycloaddition to the isocyanate and diazo precursors, and the chemistry of their breakdown products as reported by Baig G. U. and Stevens M. F. G., in an article titled "Antitumor imidazotetrazines. Part 12. Reactions of mitozolomide and its 3-alkyl congeners with oxygen, nitrogen, halogen and carbon nucleophiles", published in J. Chem. Soc. Perkin. Trans. 1 (1987), 665-670.

The original synthesis of Temozolomide involves the reaction of 5-diazoimidazole-4-carboxamide with methyl isocyanate, (see Scheme 2 below). While the reaction time in dichloromethane at 25° C. is very long (20 days), highly pure Temozolomide is obtained in high yield, as reported by Stevens M. F. G., Hickman, J. A., Stone, R., Gibson, N. W., Baig, G. U., Lunt, E., and Newton C. G., in an article titled "Antitumor Imidazotetrazines. 1. Synthesis and chemistry of 8-Carbamoyl-3-(2-chloroethyl)imidazo[5,1-d]-1,2,3,5-tetrazin-4(3H)-one, a novel broad-spectrum antitumor agent", published in J. Med. Chem. 27, 196-201, 1984.

Scheme 2

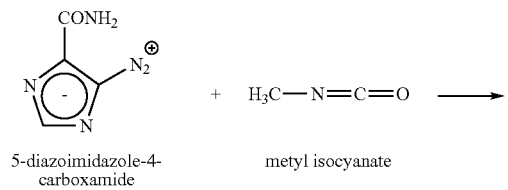

5-diazoimidazole-4-carboxamide    metyl isocyanate

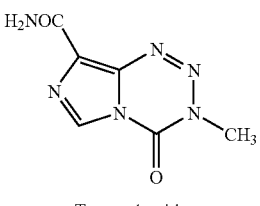

Temozolomide

A synthetic method of preparing Temozolomide, similar to the one described by Stevens et al., in J. Med. Chem. 27, 196-201, 1984, is described by Lunt et al. in U.S. Pat. No. 5,260,291.

While in both of these publications it is reported that the melting point of Temozolomide is around 210° C., Lunt also reports that upon heating "effervescence and darkening from 160° C. to 210° C." is observed. Such a behavior can be attributed to decomposition.

U.S. Pat. No. 6,844,434 describes the preparation of Temozolomide, alkyl analogs and intermediates thereof. The process, which is depicted in Scheme 3 below, comprises reacting 5-amino-1H-imidazole-4-carboxamide hydrochloride (II) with 4-nitrophenyl chloroformate to afford compound (III), which is subsequently reacted with methyl hydrazine to obtain the corresponding compound (IV), which is cyclized to yield Temozolomide.

Scheme 3

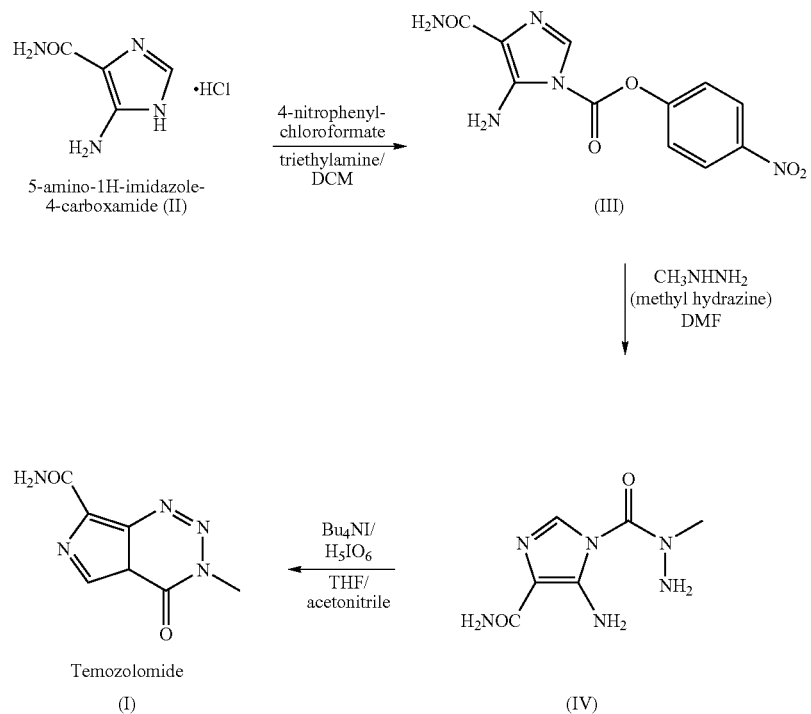

Another process for preparing Temozolomide is described in U.S. patent application having the Publication No. 2002/0095036 (see Scheme 4 below). In this process, the imine (V) is converted to 2-cyano-N-(1,1-dimethylethyl)-2-[(diphenyl-methylene)amino]-acetamide, which is converted to 2-amino-2-cyano-N-(1,1-dimethyl-ethyl)-acetamide hydrochloride. The latter is reacted with compound (VI) to obtain 5-amino-$N^4$-(1,1-dimethylethyl)-$N^1$-methyl-1H-imidazole-1,4-dicarboxamide, which is converted to 3,4-dihydro-N-(1,1-dimethylethyl)-3-methyl-imidazo-[5,1-d]-1,2,3,5-tetrazine-8-carboxamide (tert-butyl-Temozolomide), which yields Temozolomide under acidic treatment with concentrated sulfuric acid.

Yet another synthesis of Temozolomide is described by Stevens et al. in J. Org. Chem., Vol. 62, No. 21, 7288-7294, 1997, wherein Temozolomide hydrochloride salt is obtained in 65% yield by the hydrolysis of 8-cyano-3-methyl-[3H]-imidazo-[5,1-d]-tetrazin-4-one with hydrochloric acid, as shown in Scheme 5.

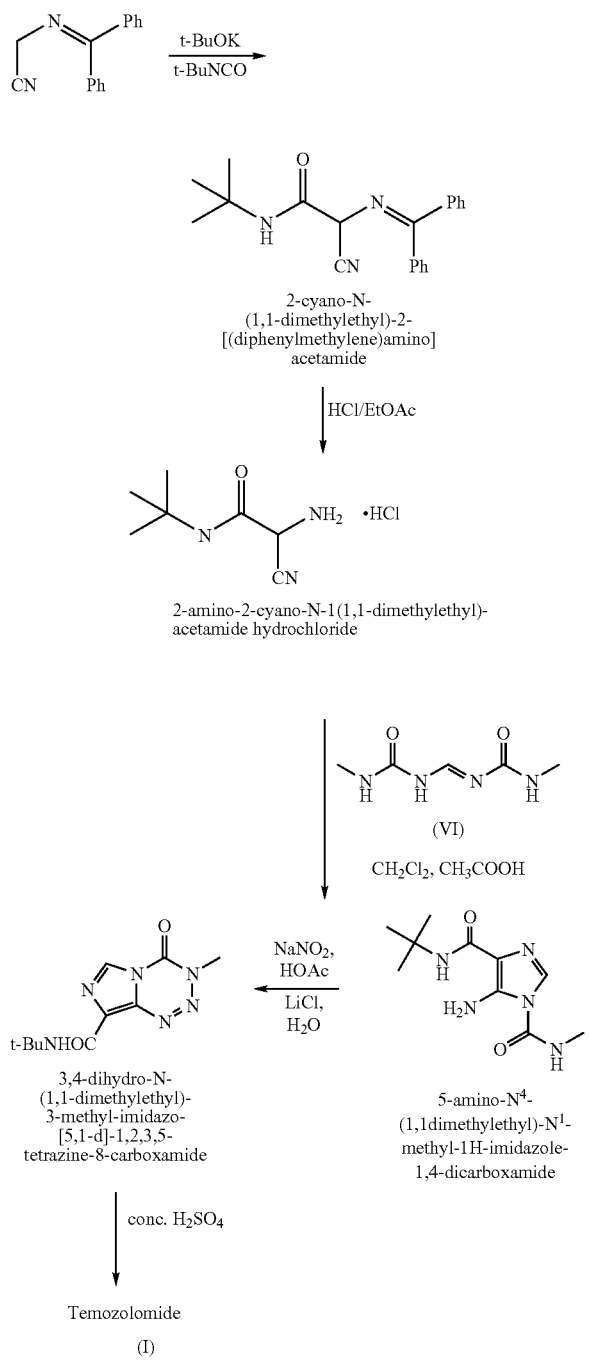

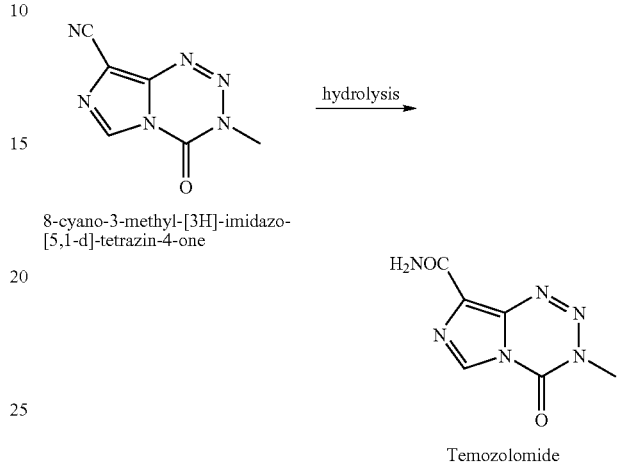

The main disadvantage of this process is the low yield in which Temozolomide hydrochloride is obtained (65%). It is assumed that the relatively elevated temperature of 60° C. used in the process increases the content of decomposition products.

The conclusion derived from the clinical trials described in detail hereinabove, is that Temozolomide is highly unstable in non-acidic pH, labile at pH>7 and stable at pH<5. Due to the intrinsic instability of Temozolomide in basic conditions, the conversion of Temozolomide hydrochloride to Temozolomide base in the usual conditions (treatment with a base) is not a viable option. Thus, there is an unmet need in the art for a simple, efficient and convenient method of converting Temozolomide hydrochloride to Temozolomide base In most of the processes for obtaining Temozolomide described above (excluding the process described by Stevens et al. in J.Org. Chem. Vol. 62, No. 21, 1997), Temozolomide is obtained as a free base, hence no further neutralization step is required.

It is known to those skilled in the art that a method of choice for converting a salt (such as the hydrochloride salt) of an organic active pharmaceutical ingredient to the corresponding free base is by dissolving the salt in a suitable solvent; adding a base (such as sodium hydroxide); and isolating the active pharmaceutical ingredient free base thus obtained, preferably by filtration.

However, this method is not applicable in the case of Temozolomide since this compound is highly unstable at basic conditions of above pH 7 and thus the use of even a milder base such as sodium bicarbonate is undesired. Furthermore, there is still a need in the art for an improved high-yield industrially convenient process for preparing highly pure Temozolomide, using conventional purification techniques, while avoiding using liquid chromatography in the last reaction step.

BRIEF SUMMARY OF THE INVENTION

The present invention provides an improved process for preparing highly pure Temozolomide base in high yield, the process comprising:
preparing Temozolomide hydrochloride; and
converting the Temozolomide hydrochloride to Temozolomide base in acidic medium.

The present invention discloses a surprising conversion of Temozolomide hydrochloride to Temozolomide free base, which is achieved in acidic pH by using a mixture of an acid (e.g., an organic acid), a water-miscible solvent, and water.

According to the present invention, the dissolution of Temozolomide hydrochloride in the mixture of acetic acid, acetonitrile, and water is complete (at pH range of 3-4), results in the precipitation of Temozolomide upon cooling.

The present invention provides also an optional step which includes a recovery stage from the purification mother liquors for preparing Temozolomide in high yield and quality Thus, in one aspect, the present invention provides an unusual conversion of Temozolomide hydrochloride to Temozolomide free base by using a mixture of acetic acid, a water miscible organic solvent, (e.g., acetonitrile), and water.

The process provided herein enables carrying out the said conversion of Temozolomide hydrochloride to Temozolomide free base in an acidic medium and thus ensures relatively high yield because of non-decomposition of Temozolomide in the acidic media, and, in addition, is a straightforward, cheap and easy to perform process.

In another aspect of the present invention, Temozolomide hydrochloride is prepared in high quality and yield by improved hydrolysis of 8-cyano-3-methyl-[3H]-imidazo-[5,1-d]-tetrazin-4-one.

According to this aspect of the present invention, the preparation of Temozolomide hydrochloride is carried out by a hydrolytic process of 8-cyano-3-methyl-[3H]-imidazo-[5,1-d]-tetrazin-4-one, using concentrated inorganic acid solution and an organic co-solvent.

DETAILED DESCRIPTION OF THE PREFERRED EMBODIMENTS

The present invention provides an improved process for preparing highly pure Temozolomide base in high yield, the process comprising:
preparing Temozolomide hydrochloride; and
converting the Temozolomide hydrochloride to Temozolomide base in acidic medium.

The present inventors have surprisingly discovered that the conversion of Temozolomide hydrochloride to Temozolomide free base can be achieved in acidic pH by using a mixture of an acid (e.g., an organic acid), a water-miscible solvent, and water.

According to one embodiment of the present invention, the organic acid is selected from the group consisting of acetic acid, propionic acid, citric acid, malonic acid, fumaric acid, malic acid, tartaric acid, oxalic acid, and the like, and combinations thereof, preferably acetic acid.

According to another embodiment of the present invention, the water-miscible solvent is selected from the group consisting of methanol, ethanol, n-propanol, isopropanol, acetone, tetrahydrofuran (THF), 2-methyltetrahydrofuran, acetonitrile, N,N-dimethylformamide (DMF), N,N-dimethylacetamide (DMA), dimethyl sulfoxide (DMSO), N-methyl-pyrrolidone (NMP), and the like, and mixtures thereof, preferably acetone, THF and ethanol and most preferably acetonitrile.

According to the present invention, the dissolution of Temozolomide hydrochloride in the mixture of acetic acid, acetonitrile, and water is complete (at pH range of 3-4), thus at the same time liberation of the salt is achieved as well as crystallization upon cooling.

Thus, in one aspect, the present invention provides an unusual conversion of Temozolomide hydrochloride to Temozolomide free base by using a mixture of acetic acid, acetonitrile, and water, as described herein.

The process described herein enables carrying out the conversion of Temozolomide hydrochloride to Temozolomide free base in acidic medium and thus ensures relatively high yield because of non-decomposition of Temozolomide in the acidic medium, and, in addition, is a straightforward, cheap and easy to perform process.

Several solvent mixtures were tested for obtaining the free Temozolomide base, as depicted in Table 1. In each case the lowest possible volume of solvent mixture needed to allow complete dissolution of Temozolomide hydrochloride was used.

While using a mixture of acetic acid, acetone, and water the obtained reaction yield was high (88%), but the ratio between Temozolomide and the volume of the solvent mixture was too high (1/24.5). In addition a somewhat colored product was obtained.

The usage of a mixture of acetic acid, acetonitrile, and water is preferable because the obtained reaction yield was high (86.7%) and the ratio between Temozolomide and the volume of the solvent mixture was the lowest (1/15), (see table 1).

TABLE 1

| | Content of the solution | | Temozolomide HCl/solvent mixture ratio (g/ml) | Process yield | Remarks |
|---|---|---|---|---|---|
| 1 | Temozolomide HCl | 11.7 g | 1/15 | 86.7% | Temozolomide was obtained in high purity of 99.96% |
| | Acetonitrile | 79 ml | | | |
| | Water | 96.5 ml | | | |
| | Acetic acid | 2.5 ml | | | |
| 2 | Temozolomide HCl | 3 g | 1/25 | Not determined | |
| | Ethanol | 33 ml | | | |
| | Water | 41.7 ml | | | |
| | Acetic acid | 0.6 ml | | | |
| 3 | Temozolomide HCl | 7.2 g | 1/24.5 | 88% | A somewhat colored product was obtained |
| | Acetone | 85 ml | | | |
| | Water | 90 ml | | | |
| | Acetic acid | 1.8 ml | | | |
| 4 | Temozolomide HCl | 2.9 g | 1/18 | 70% | Temozolomide was obtained in high purity of 99.8% |
| | THF | 23 ml | | | |
| | Water | 28.8 ml | | | |
| | Acetic acid | 0.7 ml | | | |

While the present process may be carried out at variable reaction conditions, the following typical process for the preparation of Temozolomide free base from Temozolomide hydrochloride was found to be the most preferable:
charging the reaction vessel with Temozolomide hydrochloride and a mixture of acetic acid, a water miscible organic solvent, and water;
stirring and heating the mixture to elevated temperature followed by filtering at same temperature;
cooling the solution to obtain crystals of Temozolomide free base;

filtering the crystals, washing with water and an organic solvent and drying; and optionally recovering Temozolomide from the purification mother liquor.

A suitable organic solvent for washing the obtained crystals of Temozolomide free base is selected from the group consisting of diethyl ether, diisopropyl ether, t-butyl methyl ether, acetone, methylethyl ketone, methyl acetate, ethyl acetate, n-propyl acetate, isopropyl acetate, n-butyl acetate, isobutyl acetate, tetrahydrofuran (THF), acetonitrile, and mixtures thereof, preferably acetone.

According to a preferred embodiment of the present invention, there is provided a process which optionally includes a recovery stage of Temozolomide from the purification mother liquors.

The present inventors have surprisingly discovered that by passing the solution of the purification mother liquors, obtained from crystallizations of Temozolomide hydrochloride, through a column packed with a weakly basic ion exchange resin and using the eluate in the next crystallization, the overall yield of the last reaction step of obtaining high-quality Temozolomide may be significantly increased.

While not wishing to be bound by any particular theory it is assumed that by passing the acidic purification mother liquor through the weakly basic ion exchange resin, the acid is attached to the ion exchanger, so a neutralized eluate may be collected and reused as the solvent in the next crystallization. Since the said eluate contains a certain quantity of Temozolomide base, using it as a solvent in the next crystallization causes an increase in the total yield without negatively impacting the quality.

Thus, the method of recovering highly pure Temozolomide comprises:

filling a column with an ion exchange resin, adding a solvent mixture and waiting for about 30 minutes to enable resin swelling;

allowing the solvent mixture to drain up to the top of the resin and passing the mother liquor of the previous crystallization batch through the column;

discarding the first eluted volume and then collecting the eluted solution (the eluate);

charging the reaction vessel with Temozolomide hydrochloride and the collected eluate;

stirring and heating the mixture to a relatively elevated temperature and filtering the solution at this temperature;

cooling the solution and stirring to enable crystallization;

filtering and washing with water and an organic solvent and drying; and optionally regenerating the resin and repeating the previous steps.

According to one embodiment of the present invention, the ion exchange resin is preferably a weakly basic anionic resin selected from the group consisting of Lewatit Mono Plus™ MP 64, Dowex Marathon WBA, Dowex Marathon WBA-2, Resindion A-329, Amberlite 93 and the like. The presently most preferred ion exchange resin is Lewatit Mono Plus™ MP 64.

According to another embodiment of the present invention, the preferred ratio between the resin and the volume of the loaded mother liquor solution is 1/5 (gram/ml).

According to yet another embodiment of the present invention, the organic solvent used in the mixture with water for eluting is selected from the group consisting of methanol, ethanol, n-propanol, isopropanol, acetone, tetrahydrofuran (THF), 2-methyltetrahydrofuran, acetonitrile, N,N-dimethylformamide (DMF), N,N-dimethylacetamide (DMA), dimethyl sulfoxide (DMSO), N-methyl-pyrrolidone (NMP), and mixtures thereof, preferably acetonitrile.

According to yet another embodiment of the present invention, the preferred ratio between water and acetonitrile in the said mixture is 55/45 v/v.

According to yet another embodiment of the present invention, the flow rate in which the solution is eluted through the column, which is packed with the ion exchange resin, is at least 0.2 ml/min, preferably 1 ml/min.

According to yet another embodiment of the present invention, there is provided a procedure of regenerating the resin after eluting with the solution of the mother liquor obtained from crystallization of Temozolomide hydrochloride, the procedure comprising:

washing the resin with an aqueous basic solution;

washing the resin with water;

washing the resin with a salt solution; and washing the resin again with water and checking the pH.

According to yet another embodiment of the present invention, the aqueous basic solution used for the said washing is preferably a 1% solution of NaOH.

According to yet another embodiment of the present invention, the salt solution used for the said washing is preferably an 8% solution of NaCl.

Thus, in one aspect, the present invention provides an unusual conversion of Temozolomide hydrochloride to Temozolomide free base by using a mixture of acetic acid, a water miscible organic solvent, and water as described hereinabove.

In another aspect of the present invention, Temozolomide hydrochloride is prepared in high quality and yield by an improved hydrolysis of 8-cyano-3-methyl-[3H]-imidazo-[5,1-d]-tetrazin-4-one.

According to this aspect of the present invention, the preparation of Temozolomide hydrochloride is carried out by an improved hydrolysis of 8-cyano-3-methyl-[3H]-imidazo-[5,1-d]-tetrazin-4-one, using concentrated inorganic acid solution and an organic co-solvent, the process comprising:

charging the reaction vessel with 8-cyano-3-methyl-[3H]-imidazo-[5,1-d]-tetrazin-4-one and an inorganic acid;

stirring and heating the reaction mixture to elevated temperature;

cooling the reaction mixture and adding an organic co-solvent drop-wise and stirring;

filtering the crystals of Temozolomide hydrochloride, washing with an organic solvent and drying;

According to a preferred embodiment of the present invention, an appropriate inorganic acid includes, but is not limited to, hydrochloric acid, hydrobromic acid, sulfuric acid, nitric acid, phosphoric acid, methanesulfonic acid, trifluoroacetic acid and the like, and combinations thereof, preferably hydrochloric acid. The preferred concentration of hydrochloric acid is 36.5-38% and the preferred weight/volume ratio between the starting material 8-cyano-3-methyl-[3H]-imidazo-[5,1-d]-tetrazin-4-one and hydrochloric acid is about 1/5.

The mild reaction temperature is preferably in the range of 32-35° C., which enables a clean reaction with minor amounts of impurities and high yield.

According to another embodiment of the present invention, a suitable organic co-solvent can be selected from the group consisting of methanol, ethanol, n-propanol, isopropanol, n-butanol, sec-butanol, isobutanol, acetone, methylethyl ketone, diethyl ketone, methylpropyl ketone, tetrahydrofuran (THF), acetonitrile, and mixtures thereof, preferably acetone.

The advantages of the process are the following:

A higher concentration of hydrochloric acid is used, namely 36.5-38% instead of 32%, as reported in the literature;

The reaction is carried out at a temperature of 32-35° C. instead of 60° C., thus the content of decomposition products in the final product is significantly reduced and a highly pure product is obtained without using column chromatography.

A suitable organic co-solvent is added drop-wise and as a result the reaction yield is increased to over 89% in comparison to the 65% yield reported in the literature. Thus, the process for preparing Temozolomide, including the recovery stage, yields highly pure Temozolomide having a purity of at least 98.5%, preferably over 99.5% and more preferably over 99.8%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Reference is now made to the following examples that, together with the above descriptions, illustrate the invention in a non-limiting fashion. Generally, the nomenclature used herein and the laboratory procedures utilized in the present invention include chemical and analytical techniques with which one skilled in the art is familiar. Unless otherwise defined, technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

EXAMPLES

Example 1

A 250 ml reaction vessel equipped with a magnetic stirrer and a reflux condenser was charged with 8-cyano-3-methyl-[3H]-imidazo-[5,1-d]-tetrazin-4-one (10 grams, 0.0568 mol) and hydrochloric acid (36.5-38%, 50 ml). The reaction mixture was heated to 32-35° C. and stirring was maintained at this temperature for about 3 hours. A sample was withdrawn and analyzed by HPLC to verify that the high conversion was received. (If the content of the starting material 8-cyano-3-methyl-[3H]-imidazo-[5,1-d]-tetrazin-4-one is more than 2.5% by area according to HPLC, the stirring may be continued for additional one hour).

The reaction mixture was then cooled to 20° C. and 50 ml of acetone were added drop-wise while maintaining the temperature at 20° C. Stirring was continued for 15-30 minutes. The precipitated white crystals were washed with cold acetone (20 ml) and dried at 40° C. in vacuum to obtain 11.7 grams (0.0507 mol) of Temozolomide hydrochloride (89.3% yield). Purity (by HPLC): 99.6%.

Example 2

A 500 ml reaction vessel equipped with a magnetic stirrer and a reflux condenser was charged with Temozolomide hydrochloride (11.7 grams, 0.0507 mol), acetonitrile (79 ml), acetic acid (2.5 ml) and water (96.5 ml). The reaction mixture was heated to 60-63° C. and stirring was maintained at this temperature for about 10 minutes. The reaction mixture was filtered at this temperature and then cooled to 5° C. for about half an hour to enable crystallization. The crystals thus obtained were collected and washed with water (2×20 ml) and cold acetone (20 ml). The crystals were dried at 40° C. in vacuum to obtain 8.54 grams (0.044 mol) of free Temozolomide base (86.7% yield). Purity (by HPLC): 99.96%.

Example 3

A 500 ml reaction vessel equipped with a magnetic stirrer and a reflux condenser was charged with Temozolomide hydrochloride (7.2 gram, 0.031 mol), acetone (85 ml), acetic acid (1.8 ml) and water (90 ml). The reaction mixture was heated to reflux and stirring was maintained at this temperature for about 10 minutes. The reaction mixture was filtered at elevated temperature and then cooled to 5° C. for about half an hour to enable crystallization. The crystals thus obtained were collected and washed with water (2×20 ml) and cold acetone (20 ml). The crystals were dried at 40° C. in vacuum to obtain 5.3 grams (0.027 mol) of free Temozolomide base (88% yield).

Example 4

A 250 ml reaction vessel equipped with a magnetic stirrer and a reflux condenser was charged with Temozolomide hydrochloride (2.9 grams, 0.0126 mol), THF (23 ml), acetic acid (0.7 ml) and water (28.8 ml). The reaction mixture was heated to reflux and stirring was maintained at this temperature for about 10 minutes. The reaction mixture was filtered at elevated temperature and then cooled to 5° C. for about half an hour to enable crystallization. The crystals thus obtained were collected and washed with water (2×20 ml) and cold acetone (20 ml). The crystals were dried at 40° C. in vacuum to obtain 1.71 grams (0.0088 mol) of free Temozolomide base (70% yield). Purity (by HPLC): 99.8%.

Example 5

A 1.25 cm width column was filled with 10 grams of the ion exchange resin Lewatit Mono Plus™ MP-64. A solvent mixture comprising 55% water and 45% acetonitrile (20 ml) was added and 30 minutes were allowed for resin swelling. Then, the solution was allowed to drain up to the top of the resin and a solution of the mother liquor of example 1 (50 ml) was passed through the column at a rate of about 1 ml/1 min. The first volume was discarded (10 ml) and then the eluted solution (the eluate) was collected (50 ml) and transferred to a reaction vessel. Temozolomide hydrochloride (3.33 grams, 0.0144 moles) was added and the mixture was heated to 60-63° C. under stirring and filtered at this temperature. Then, the mixture was cooled to 5° C., and stirring was maintained for about 30 minutes to enable crystallization. The crystals thus obtained were collected by filtration and washed with water (2×10 ml) and cold acetone (10 ml). The crystals were dried at 40° C. in vacuum to obtain 2.52 grams (0.013 moles) of Temozolomide base in 90.3% yield. Purity (by HPLC): 99.9%.

Example 6

The regeneration of the ion exchange resin was carried out by washing it with 1% NaOH 1% (100 ml), then with water (50 ml) followed by washing with NaCl 8% solution (50 ml) and again with water (100 ml). The pH was checked (pH~8).

What is claimed is:

1. A process for preparing Temozolomide base, the process comprising:
    contacting Temozolomide hydrochloride with at least one organic acid to produce Temozolomide base; and
    isolating the Temozolomide base.

2. The process of claim 1, wherein the Temozolomide hydrochloride is contacted with the organic acid in a mixture of at least one water miscible organic solvent and water.

3. The process of claim 1, wherein the process comprises:
    charging a reaction vessel with the Temozolomide hydrochloride, the at least one organic acid, at least one water miscible organic solvent, and water to form a mixture;
    heating the mixture to an elevated temperature to form a solution and filtering the solution at an elevated temperature;
    cooling the solution to form crystals of Temozolomide free base and a mother liquor;
    filtering to separate the crystals from the mother liquor, washing the crystals with a mixture of water and at least one organic solvent and drying the crystals; and
    optionally recovering additional Temozolomide free base from the mother liquor.

4. The process of claim 3, wherein the at least one water miscible organic solvent is selected from methanol, ethanol, n-propanol, isopropanol, acetone, tetrahydrofuran (THF), 2-methyltetrahydrohan, acetonitrile, N,N-dimethylformamide (DMF), N,N-dimethylacetamide (DMA), dimethyl sulfoxide (DMSO), N-methyl-pyrrolidone (NMP), and mixtures thereof.

5. The process of claim 4, wherein the at least one water miscible organic solvent is acetone, THF, ethanol, or acetonitrile.

6. The process of claim 3, wherein the at least one organic acid is selected from acetic acid, propionic acid, citric acid, malonic acid, fumaric acid, malic acid, tartaric acid, oxalic acid, and combinations thereof.

7. The process of claim 6, wherein the organic acid is acetic acid.

8. The process of claim 3, wherein said elevated temperature is from about 40° C. to about 80° C.

9. The process of claim 3, wherein the organic solvent used for washing the crystals of Temozolomide free base is selected from diethyl ether, diisopropyl ether, t-butyl methyl ether, acetone, methylethyl ketone, methyl acetate, ethyl acetate, n-propyl acetate, isopropyl acetate, n-butyl acetate, isobutyl acetate, tetrahydrofuran (THF), acetonitrile, and mixtures thereof.

10. The process of claim 9, wherein the organic solvent used for washing the crystals of Temozolomide free base is acetone.

11. A method for preparing Temozolomide free base, the method comprising:
    producing a mother liquor according to claim 3;
    eluting the mother liquor through a column containing a weakly basic ion exchange resin, to produce an eluate containing Temozolomide free base;
    combining Temozolomide hydrochloride with the eluate to produce a mixture of the eluate and Temozolomide hydrochloride;
    heating the mixture to an elevated temperature to produce a solution, and filtering the solution at an elevated temperature;
    cooling the solution to crystallize Temozolomide free base;
    filtering the crystals, washing the crystals with a mixture of water and at least one organic solvent and drying the crystals; and
    optionally regenerating the resin and repeating the previous steps.

12. The method of claim 11, wherein the ion exchange resin is a weakly basic anionic resin selected from Lewatit Mono Plus™ MP 64, Dowex Marathon WBA, Dowex Marathon WBA-2, Resindion A-329, and Amberlite 93.

13. The method of claim 12, wherein the ion exchange resin is Lewatit Mono Plus™ MP 64, and the ratio between the resin and the volume of the loaded mother liquor solution is about 1/5 (gram/ml).

14. The method of claim 11, wherein the mother liquor is eluted with a solvent selected from methanol, ethanol, n-propanol, isopropanol, n-butanol, sec-butanol, acetone, methylethyl ketone, diethyl ketone, methylpropyl ketone, tetrahydrofuran (THF), acetonitrile, and mixtures thereof.

15. The method of claim 14, wherein the mother liquor is eluted with a mixture of water and acetonitrile, wherein the ratio between the water and the acetonitrile is 55/45 v/v.

16. The method of claim 11, further comprising regenerating the resin after eluting the mother liquor.

17. The method of claim 16, wherein the the regeneration comprises washing the resin with a 1% solution of NaOH and washing the resin with an 8% solution of NaCl.

18. The process of claim 3, wherein the product is obtained in about 90% yield, and in a purity of at least 98.5%.

19. The process of claim 3, wherein the product is obtained in about 90% yield, and in a purity over 99.8%.

20. The process of claim 1, further comprising preparing the Temozolomide hydrochloride by hydrolyzing 8-cyano-3-methyl-[3H]-imidazo-[5,1-d]-tetrazin-4-one with aqueous hydrochloric acid, to thereby produce a reaction mixture containing Temozolomide hydrochloride,
    adding an organic solvent to the reaction mixture to thereby produce crystals of Temozolomide HCl;
    filtering the crystals of Temozolomide HCl, washing the crystals with an organic solvent and drying the crystals.

21. The process of claim 20, wherein the aqueous hydrochloric acid reagent has a concentration of from 36.5-38% and the weight/volume ratio between the starting material 8-cyano-3-methyl-[3H]-imidazo-[5,1-di-tetrazin-4-one and the hydrochloric acid solution is about 1/5 gram/ml.

22. The process of claim 20, wherein the organic solvent in the reaction mixture is selected from methanol, ethanol, n-propanol, isopropanol, n-butanol, secbutanol, isobutanol, acetone, methylethyl ketone, diethyl ketone, methylpropyl ketone, tetrahydrofuran (THF), acetonitrile, and mixtures thereof.

23. The process of claim 22, wherein the organic solvent is acetone.

24. The process of claim 20, wherein the hydrolysis is carried out at a temperature of from 32-35° C.

25. The process of claim 20, wherein the purity of Temozolomide hydrochloride obtained is at least 98.5% (by HPLC).

26. The process of claim 20, wherein the purity of Temozolomide hydrochloride obtained is at least 99.5% (by HPLC).

* * * * *